US011776375B2

(12) United States Patent
Rofe et al.

(10) Patent No.: US 11,776,375 B2
(45) Date of Patent: Oct. 3, 2023

(54) PRESSURE SENSING MAT WITH VENT HOLES

(71) Applicant: Wellsense, Inc., Birmingham, MI (US)

(72) Inventors: Arik Rofe, Ma'ale HaHamisha (IL); Oola Greenwald, Mevasseret Zion (IL); Roman S. Ferber, Birmingham, MI (US); Asaf Brosch, Rosh Tzurim (IL)

(73) Assignee: Wellsense, Inc., Birmingham, MI (US)

( * ) Notice: Subject to any disclaimer, the term of this patent is extended or adjusted under 35 U.S.C. 154(b) by 25 days.

(21) Appl. No.: 17/571,972

(22) Filed: Jan. 10, 2022

(65) Prior Publication Data

US 2023/0218233 A1    Jul. 13, 2023

(51) Int. Cl.
*G08B 21/04* (2006.01)
*A61B 5/00* (2006.01)

(52) U.S. Cl.
CPC ......... *G08B 21/0461* (2013.01); *G08B 21/04* (2013.01); *A61B 5/6892* (2013.01); *A61B 2562/0247* (2013.01); *A61B 2562/046* (2013.01); *G08B 21/0438* (2013.01)

(58) Field of Classification Search
CPC ........ G08B 21/00; G08B 21/02; G08B 21/04; G08B 21/0438; G08B 21/0461; G08B 21/22; G01D 5/165; A61B 5/00; A61B 5/11; G01L 1/20; G01L 1/205; G01L 1/22; G01L 3/00
See application file for complete search history.

(56) References Cited

U.S. PATENT DOCUMENTS

| 7,695,597 B1 * | 4/2010 | Drewery | C25F 7/00 204/194 |
| 8,161,826 B1 * | 4/2012 | Taylor | A47C 27/082 73/862.041 |
| 9,823,141 B2 | 11/2017 | Li et al. | |

(Continued)

FOREIGN PATENT DOCUMENTS

| CA | 213641864 | * | 7/2021 |
| WO | 2021071370 A1 | | 4/2021 |
| WO | 2020172662 A1 | | 9/2021 |

OTHER PUBLICATIONS

NPL search (Mar. 23, 2023).*

*Primary Examiner* — Van T Trieu
(74) *Attorney, Agent, or Firm* — Brooks Kushman P.C.

(57) ABSTRACT

A pressure sensing mat having first and second conductive layers and an insulative layer. The first conductive layer defines a first aperture and includes first spaced apart conductive regions and first non-conductive regions therebetween. The first spaced apart conductive regions and non-conductive regions extends in a first direction. The second conductive layer defines a second aperture and includes second spaced apart conductive regions and second non-conductive regions therebetween. The second spaced apart conductive regions and the second non-conductive regions extend in a second direction different than the first direction. The insulative layer is between the first and second conductive layers and defines a third aperture. The first, second, and third apertures are aligned with each other such that the first, second, and third apertures form a vent through the first and second conductive layers and the insulative layer.

20 Claims, 8 Drawing Sheets

(56) References Cited

U.S. PATENT DOCUMENTS

| | | | |
|---|---|---|---|
| 10,386,224 B2 | 8/2019 | Shim et al. | |
| 10,416,031 B2 | 9/2019 | Hsu et al. | |
| 10,856,737 B2 | 12/2020 | Au et al. | |
| 2002/0143373 A1 | 10/2002 | Courtnage et al. | |
| 2006/0213286 A1 | 9/2006 | Chasco Perez De Arenaza | |
| 2008/0265393 A1* | 10/2008 | Lin | H01L 24/83 |
| | | | 438/118 |
| 2014/0373594 A1 | 12/2014 | Remez et al. | |
| 2016/0327441 A1 | 11/2016 | Iwase et al. | |
| 2019/0137322 A1 | 5/2019 | Choi et al. | |
| 2019/0197865 A1* | 6/2019 | Lu | G08B 21/0461 |

\* cited by examiner

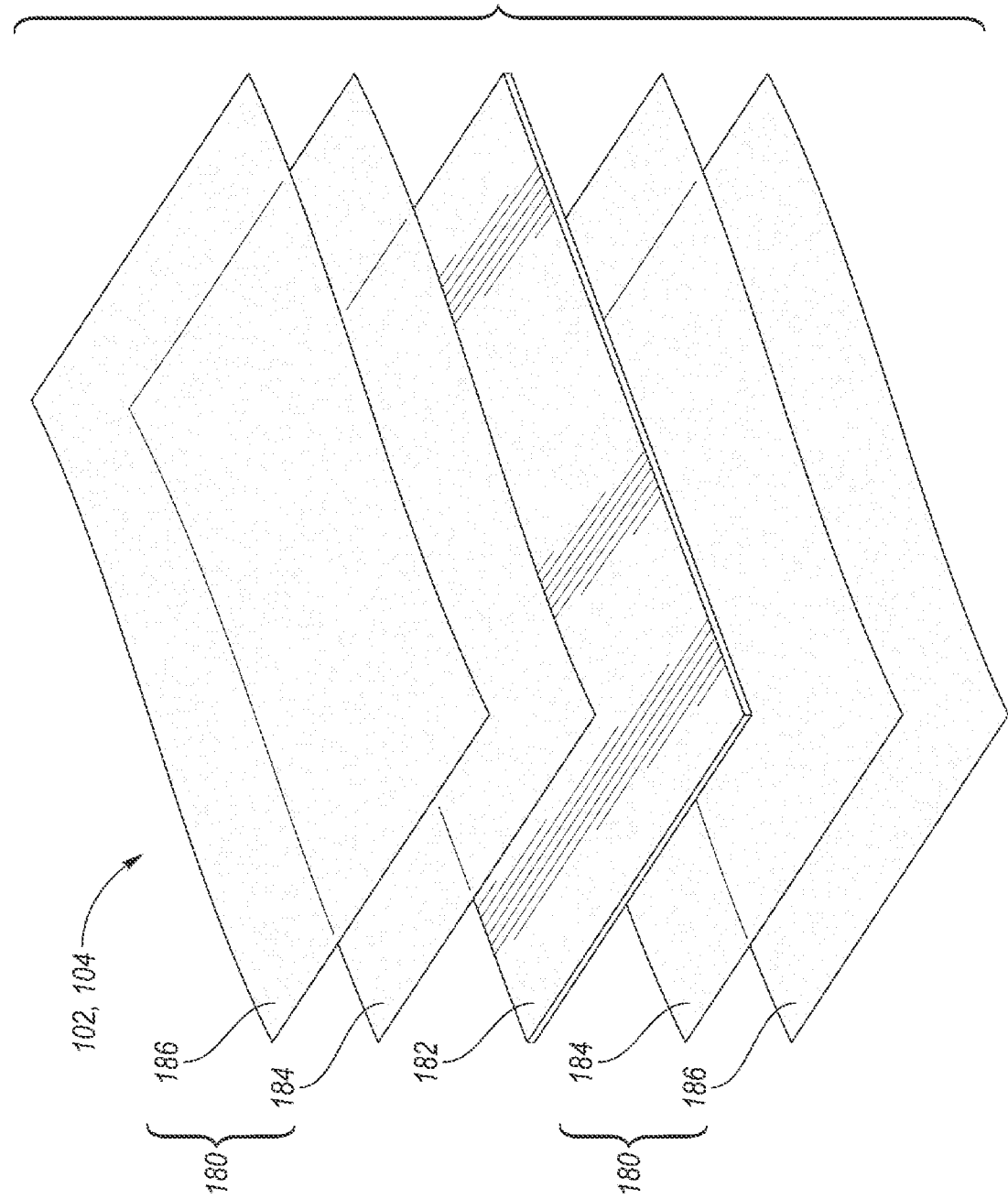

PRESSURE SENSING MAT WITH VENT HOLES

TECHNICAL FIELD

Aspects of the disclosure generally relate to a pressure sensing mat configured to aid in the mitigation of pressure injuries, otherwise known as decubitus ulcers.

BACKGROUND

Pressure injuries, otherwise known as decubitus ulcers, pressure ulcers or bedsores, are lesions developed when a localized area of soft tissue of a subject is compressed between a bony prominence and an external surface for a prolonged time. Pressure injuries could appear in various areas of the body, such as elbows, knees, pelvis, lower back, and ankles. Development of pressure injuries are based on a combination of factors, such as, unrelieved pressure, friction, shearing forces, humidity, and temperature.

Patients lying in hospital beds and other surfaces often suffer from pressure injuries. Pressure injuries are a risk for patients in different hospital departments. For instance, pressure injuries may be an issue for patients lying on an operating table during an operation. Patients lying in hospital beds in other departments (e.g., intensive care unit, neo natal care unit, step down units, etc.) are also prone to pressure injuries. However, pressure injuries are not limited to hospitalized patients. Individuals confined to wheelchairs are prone to suffer from pressure injuries, especially in their pelvis, lower back, and ankles. Nursing and rehabilitation home residents also can suffer from pressure injuries. Therefore, there is a relatively large number of settings within the hospital and in other environments where individuals may encounter problems with pressure injuries.

Although easily preventable or treatable if found early, if a pressure injury lingers, it becomes painful and treatment is both difficult and expensive. In many cases, pressure injuries can prove fatal, even under the auspices of medical care. According to one estimate, 2.5 million people suffer from pressure injuries in the United States each year, resulting in over 60,000 deaths annually. Pressure sensing mats have been utilized in hospital bed settings to aid in the mitigation of pressure injuries. The pressure sensing mats use capacitive or resistive sensors to track the pressure exerted on different regions of the body of a patient lying in the hospital bed.

SUMMARY

According to one embodiment, a pressure sensing mat is disclosed. The pressure sensing mat may include a first conductive layer, a second conductive layer, and an insulative layer that may be disposed between the first and second conductive layers. The first conductive layer may include a first plurality of spaced apart conductive regions and a first plurality of non-conductive regions that may be disposed therebetween. The first plurality of spaced apart conductive regions and the first plurality of non-conductive regions may extend in a first direction and the first conductive layer may define a first aperture. The second conductive layer may include a second plurality of spaced apart conductive regions and a second plurality of non-conductive regions that may be disposed therebetween. The second plurality of spaced apart conductive regions and the first plurality of non-conductive regions may extend in a second direction that may be different than the first direction. The second conductive layer may define a second aperture. The insulative layer may define a third aperture. The first, second and third apertures may be aligned with each other such that the first, second and third apertures form a vent through the first and second conductive layers and the insulative layer.

The first aperture may include a first pattern of apertures, the second aperture may include a second pattern of apertures, and the third aperture may include a third pattern of apertures. The first, second and third patterns of apertures may form a plurality of vents that may extend through the first and second conductive layers and the insulative layer.

The first, second and third apertures may have first, second and third profiles, respectively. The first, second and third profiles may be substantially congruent.

The pressure sensing mat may include a first protective layer and a second protective layer. The first protective layer may define a first protective layer aperture and may be adjacent to the first conductive layer. The second protective layer may be adjacent to the first conductive layer and may define a second protective layer aperture. The first and second protective layers may be first and second outer layers, respectively.

According to another embodiment, a pressure sensing mat is disclosed. The pressure sensing mat may include a first conductive layer, a second conductive layer, an insulative layer, a first protective layer, and a second protective layer. The first conductive layer may include a first plurality of spaced apart conductive regions and a first plurality of non-conductive regions that may be disposed therebetween. The first plurality of spaced apart conductive regions and the first plurality of non-conductive regions may extend in a first direction and the first conductive layer may define a first aperture. The second conductive layer may include a second plurality of spaced apart conductive regions and a second plurality of non-conductive regions that may be disposed therebetween. The second plurality of spaced apart conductive regions and the first plurality of non-conductive regions may extend in a second direction that may be different than the first direction. The second conductive layer may define a second aperture. The insulative layer may be disposed between the first and second conductive layers and may define a third aperture. The first protective layer may be adjacent to the first conductive layer and may define a first protective layer aperture. The second protective layer may be adjacent to the second conductive layer and may define a second protective layer aperture.

The first protective layer aperture and the second protective layer aperture may be diametrically smaller than the first aperture, the second aperture, and the third aperture.

The first, second, and third apertures and the first and second protective layer apertures may form a vent that may have a sealed circumference that may be configured to inhibit penetration of water and/or vapor into the first and second conductive layers and the insulative layer.

The sealed circumference may include co-minglingly joined circumferential areas of the first aperture, the second aperture, and the third aperture and the first protective layer aperture and the second protective layer aperture.

The sealed circumference may include ultrasonically soldered circumferential areas of the of the first aperture, the second aperture, and the third aperture and the first protective layer aperture and the second protective layer aperture.

According to yet another embodiment, a pressure sensing mat is disclosed. The pressure sensing mat may include a first conductive layer, a second conductive layer, an insulative layer, a first protective layer, a second protective layer, and a cover. The first conductive layer may include a first plurality of spaced apart conductive regions and a first plurality of non-conductive regions that may be disposed therebetween. The first plurality of spaced apart conductive regions and the first plurality of non-conductive regions may extend in a first direction and the first conductive layer may define a first aperture. The second conductive layer may include a second plurality of spaced apart conductive regions and a second plurality of non-conductive regions that may be disposed therebetween. The second plurality of spaced apart conductive regions and the first plurality of non-conductive regions may extend in a second direction that may be different than the first direction. The insulative layer may be disposed between the first and second conductive layers and may define a third aperture. The first protective layer may be adjacent to the first conductive layer and may define a first protective layer aperture. The second protective layer may be adjacent to the second conductive layer and may define a second protective layer aperture. The first, second, and third apertures and the first and second protective layer apertures may collectively form a vent. The cover may at least partially cover the first protective layer and may be formed of a moisture permeable material configured to transmit moisture and/or fluid from an outer surface of the cover to the vent.

The first and second protective layers may each be moisture impermeable. The first and second conductive layers may be adhered to the insulative layer. The first protective layer may be adhered to the first conductive layer.

BRIEF DESCRIPTION OF THE DRAWINGS

FIG. 7 depicts a fragmented, exploded, and perspective schematic view of an exemplary pressure sensing mat.

DETAILED DESCRIPTION

Figure 1:
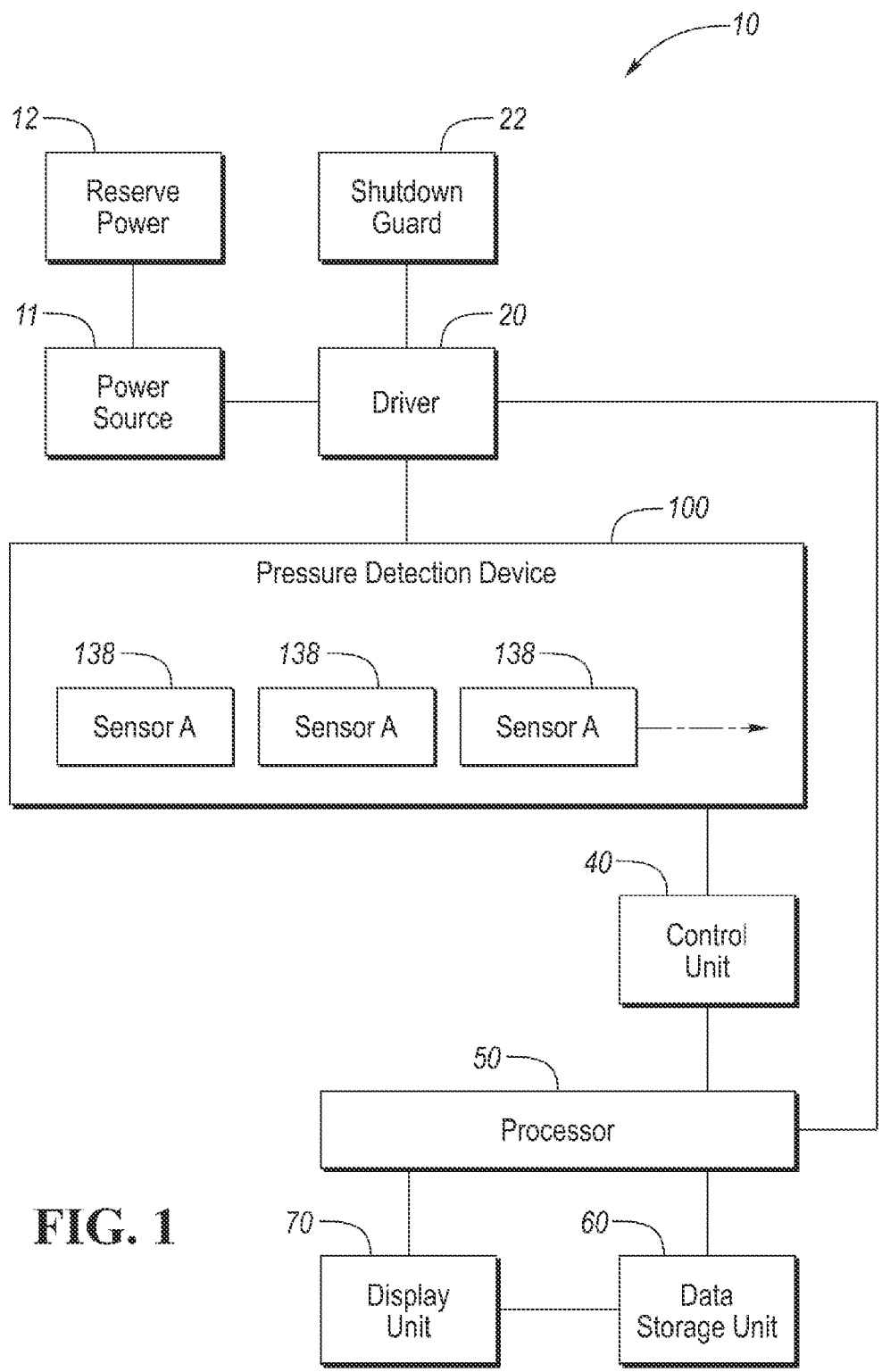
FIG. 1 is a schematic of the main components of a pressure sensing mat and related components of at least one embodiment.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

As used in the specification and the appended claims, the singular form "a," "an," and "the" comprise plural referents unless the context clearly indicates otherwise. For example, reference to a component in the singular is intended to comprise a plurality of components.

The term "substantially" or "about" may be used herein to describe disclosed or claimed embodiments. The term "substantially" or "about" may modify a value or relative characteristic disclosed or claimed in the present disclosure. In such instances, "substantially" or "about" may signify that the value or relative characteristic it modifies is within ±0%, 0.1%, 0.5%, 1%, 2%, 3%, 4%, 5% or 10% of the value or relative characteristic.

The terms "fixed to" may be used herein to describe disclosed or claimed embodiments. The term "fixed to" may refer to a molecular bond or a mechanical bond between two or more portions or components of the mat. A molecular bond, also known as a covalent bond, may be formed by acting upon one or more components, having similar or dissimilar material, to be joined so that atoms of each component are bound by sharing pairs of electrons between the two components. The molecular bond may be formed by melting one or more portions of the mating surfaces so that one component is joined to another. This may be formed by ultrasonic welding, heat staking, or another suitable process as required. A mechanical bond may refer to one or more component surfaces that have retention or engagement features that interface with retention or engagement features of the other component to fix the two components to one another. The percentages of interfacing surfaces that contact each other is in the range of 50% to 100%. As another example, a mechanical bond may be formed by one or more adhesives disposed between the two or more portions of components to be joined.

Aspects of the disclosure generally relate to a capacitive pressure sensing mat configured to aid in the mitigation of pressure injuries. Other capacitive pressure sensing mats have been proposed. In one previous implementation, the pressure mat is composed of a matrix of knitted conductive fabric spaced apart by an insulator and connected by a woven ribbon to form a plurality of electrical capacitors. The knitted conductive fabric matrix is produced by standard processes associated with textile manufacturing. The material and manufacturing processes for these knitted conductive fabric pressure sensing mats may be costly thus requiring them to be reused several times to make their use economically feasible. Reusing the pressure mat may require the mat to be cleaned and sanitized after each use and may create sanitation issues of the mat is not sufficiently cleaned or sanitized between patients. Also, these knitted conductive fabric pressure sensing are specially designed and manufactured for different operating environments, e.g., intensive care units, operating rooms, nursing homes, wheelchairs. Therefore, in some instances, these pressure sensing mats may not be suitable as a modular solution.

Pressure mats composed of knitted fabric often involve individual calibration for accuracy and precision. Knitted fabrics include conductive threads or yarns that are relatively elastic and deformable. Available pressure mats are calibrated before use. During the calibration process, the capacitance of each sensor in the matrix is measured for one or more known pressures. The functional relationship between the known pressures and measured capacitance at each sensor is used to calibrate each sensor. Geometrical tolerances of knitted fabrics may have a relatively large range, e.g., 0.5 mm to 1.5 mm, thereby adding variability to the capacitance measurements.

The capacitive pressure sensing mat of the present disclosure may be formed of spaced apart laminated conductive sheets. The geometrical tolerances of the laminated conductive sheets may have relatively smaller range, e.g., 0.5 microns to 2 microns, than the knitted fabric matrix.

Because the laminated conductive sheets have a narrower tolerance band as compared to pressure mats composed of knitted fabrics, calibration may be streamlined relative to sensing mats composed of knitted fabrics. In some instances, the use of laminated conductive sheets may obviate the need to calibrate every pressure mat before each pressure mat is used. As one example, a statistical analysis for a predetermined number of pressure mats may be used to determine the required frequency of calibrating the pressure mats composed of laminated conductive sheets. Decreasing the frequency and quantity of calibration processes may create efficiencies in manufacturing and may reduce costs.

One or more of the capacitive pressure sensing mats of the present disclosure may include relatively inelastic material such as laminated conductive sheets that may mitigate relative movement between two or more layers and two or more sensors of the sheet as compared to known pressure mats composed of knitted fabrics. The knitted fabrics over time may begin to elongate and such elongation may reduce the useful life of the pressure mat. The relatively inelastic material of the pressure mat of the present disclosure may last longer by avoiding this potential issue.

Available pressure sensing mats are typically plugged into a power source and connected to a computer or controller to collect the measured data. One or more of the capacitive pressure sensing mats of the present disclosure may be configured for wireless power and communication. The capacitive pressure sensing mats of the present disclosure may be capable of communicating with a wireless network and powered by a rechargeable battery. The capacitive pressure sensing mats of the present disclosure may be configured to be disposable for use in the operating room. The pressure sensing mats of the present disclosure may be adaptable to a modular manufacturing method where the laminated sheet material may be cut to different sizes from the same stock material so that the laminated conductive sheets can be applied to many different use cases and settings. The pressure sensing mats disclosed in embodiments of the present disclosure provides one or more technical solutions to one or more of the technical drawbacks of the currently proposed pressure sensing mats.

Referring generally to the figures, a pressure sensing mat 100 is provided. The pressure sensing mat 100 may include a first conductive layer 102, a second conductive layer 104, an insulative layer 106, a first protective layer 108, a second protective layer 110, and a cover 112. The first conductive layer 102 may include first spaced apart conductive regions 114 and first non-conductive regions 116 that may be disposed therebetween. The first spaced apart conductive regions 114 and first non-conductive regions 116 may extend in a first direction D1 and the first conductive layer may define first apertures 118.

The second conductive layer 104 may include second spaced apart conductive regions 120 and second non-conductive regions 122 that may be disposed therebetween. The second conductive layer 104 may define second apertures 124. The second spaced apart conductive regions 120 and the first non-conductive regions 122 may extend in a second direction D2 that may be different than the first direction D1. As an example, the second direction D2 may be substantially orthogonal to the first direction D1.

The insulative layer 106 may be disposed between the first and second conductive layers 102, 104 and may define a third apertures 126. The first protective layer 108 may be adjacent to the first conductive layer 102 and may define first protective layer apertures 128. The second protective layer 110 may be adjacent to the second conductive layer 104 and may define second protective layer apertures 130. One or more of the first apertures 118, the second apertures 124, and the third apertures 126 and the first and second protective layer apertures 128 and 130 may collectively form a vent 132.

The first conductive layer 102 and the second conductive layer 104 may each define interstices 134 that may form arrays of conductive cells 136. The conductive cells 136 of the first conductive layer 102 may be substantially aligned with the conductive cells 136 of the second conductive layer 104 to form a matrix or array of capacitors 138. Each conductive layer 102, 104 may include conductive leads 140 that, combined with conductive cells 136 that are aligned with one another, form a conductive path 142. The conductive paths 142 of the first conductive layer 102 may be arranged substantially orthogonal to the conductive paths 142 of the second conductive layer 104 to form the matrix of capacitors 138.

The cover 112 may at least partially cover the first protective layer 108 and may be formed of a moisture permeable material configured to transmit moisture and/or fluid from an outer surface 144 of the cover 112 to the vent 132. As an example, the material may be configured to absorb or draw off fluids including but not limited to perspiration, urine, and blood from a user disposed on the mat. These and other fluids may be drawn off by capillary action that may facilitate moving the fluids from the outer surface 144 through the cover 112, to one or more of the protective layers 108, 110 and to the one or more of the vents 132.

Referring to the block diagram of FIG. 1, an embodiment of a pressure sensing may system 10 is depicted. The system 10 may include at least one pressure sensing mat 100 including a plurality of sensors such as capacitors 138, a driver 20, a control unit 40 which may be connected to a power source 11, a processor 50, a data storage unit 60 and a display unit 70. Power may be supplied via a power cord connected to a wall outlet, or via battery power, optionally rechargeable. Battery support also allows for movement of the bed without requiring a powering off of the system 10. As a safety measure and for compliance tracking, caregiver authentication may be required via a shutdown guard 22 to confirm powering off of the control unit 40, such as with entry of a caregiver's employee identification number. While the system identified in FIG. 1 is a capacitive sensor system, in other embodiments, other methods can be utilized, such as resistive or piezoresistive systems.

The capacitors 138 may be arranged at different locations on the pressure sensing mat 100. In an example, the capacitors 138 may be arranged in a two-dimensional grid across the surface of the pressure sensing mat 100. The driver 20 may be configured to supply voltage to the capacitors 138 in the pressure sensing mat 100, and the processor 50 may measure the potential across the capacitors 138, calculate impedance values for each capacitor 138, and store the data in a data storage unit 60. The stored data may be further processed, analyzed, and displayed on the display unit 70, such as a computer screen, laptop, personal digital assistant (PDA), tablet device, mobile phone screen, printed sheet, or integrated display screen. Although presented in the block diagram of FIG. 1 as separate blocks, the system 10 may optionally be integrated into a stand-alone system.

Figure 2:
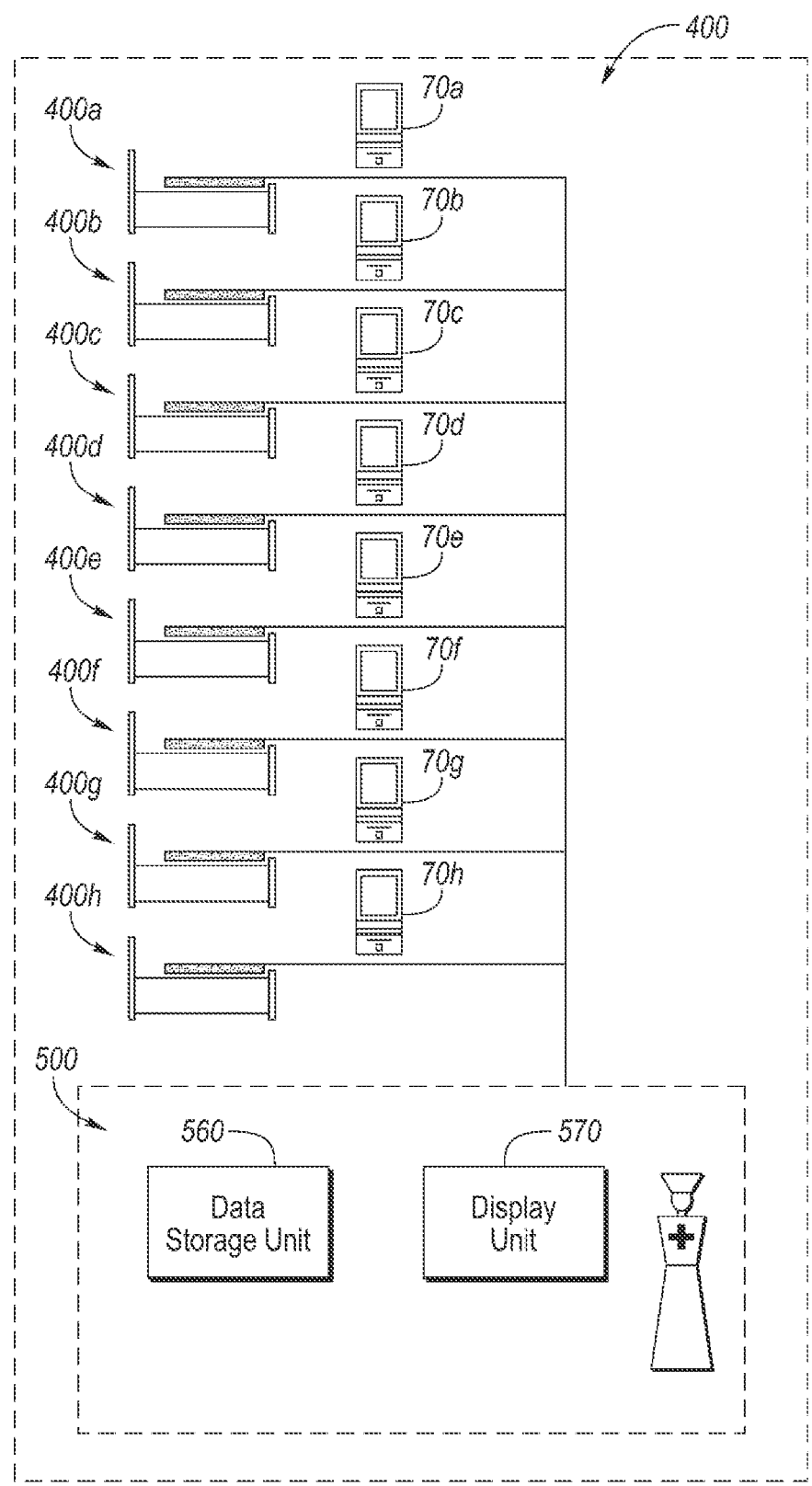
FIG. 2 is a schematic of an individual care environment according to at least one embodiment.

Referring now to FIG. 2, an individual care environment 400 may include sub-systems 400a through 400h in communication with a common remote-control center 500. The individual care environment 400 may be in a hospital, nursing home, home care or rehabilitative care environment, as examples. If the individual care environment 400 is a hospital, the common remote-control center 500 may be a nursing station. As shown in FIG. 1, each of the sub-systems 400*a* through 400*h* includes a bed. The sub-systems 400*a* through 400*h* may be configured to communicate with the common remote-control center 500, for example at a nursing station. This communication can be provided via wiring to a nurse call system, or alternatively via wireless communication (e.g., BLUETOOTH, ZIGBEE, Wi-Fi, cellular, etc.) to the nursing station. Alternatively, the sub-systems 400*a* through 400*h* may be located remotely from one another, for example each in an individual home, and the remote-control center 500 may be a manned observation station.

Figure 3:
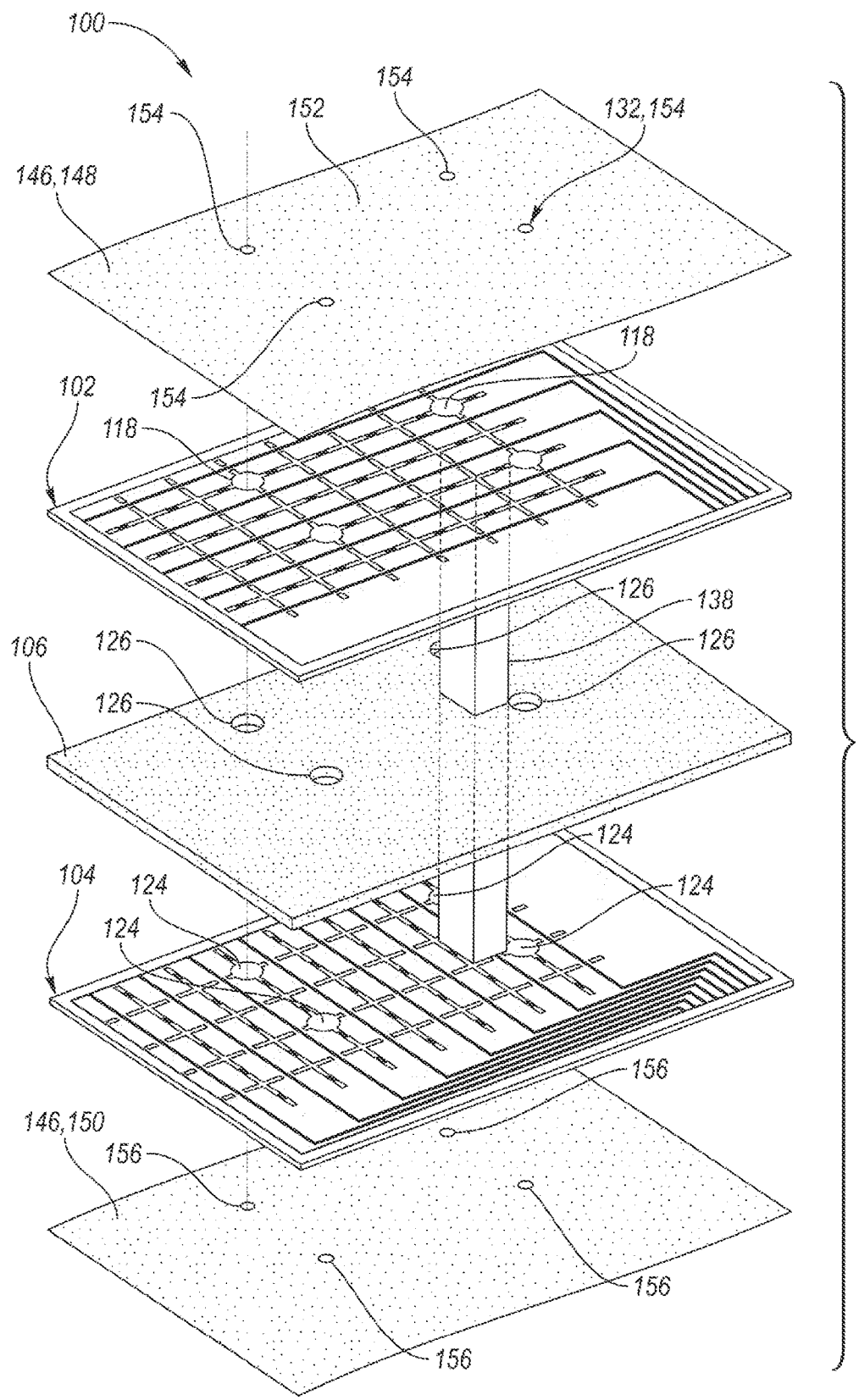
FIGS. 3 and 4 depict a fragmented, exploded, perspective, and schematic views of multiple embodiments of pressure sensing mats.

Referring to FIG. 3, the pressure sensing mat 100 according to one or more embodiments is provided. A cover 146 may include a top cover 148, positioned above the first conductive layer 102, and a bottom cover 150 positioned below the second conductive layer 104. As an example, the top cover 148 and bottom cover 150 may be joined at one or more seams by a zipper or other materials as required. The top cover 148 and the bottom cover 150 may extend the longevity of the pressure sensing mat 100 and may serve to protect the conductive layers 102 and 104 from tearing or puncturing.

In one or more embodiments, the cover 146 may be formed of a woven or non-woven fabric that may form a body-facing surface 152. For example, in some embodiments, the fabric that forms the body-facing surface 152 may be a wicking fabric. As used herein in one or more embodiments, the term "wicking fabric" refers to a fabric having a surface that becomes wet and, e.g., spreads the fluid across the fabric. In some embodiments, the body-facing surface 152 of the fabric may be coated, dipped, or printed with a wicking compound, that may serve to enhance wicking and moisture dispersal throughout all or a portion of the cover 146. Specific, non-limiting examples of wicking compounds of use include copolymers of polyethylene glycol and polyethylene terephthalate, and dilute solutions of hydrophilic polyurethane.

In one or more embodiments, the body-facing surface 152 may be formed by a fluid or moisture impermeable material. The material may be non-porous or micro-porous and may serve to prevent fluids from dispersing through the cover 146 to the first conductive layer 102, or second conductive layer 104, or both, to prevent an electric short or another event that may render the pressure sensing mat 100 inoperable. As one example, the cover 146 may be composed of polytetrafluoroethylene (PTFE) or expanded PTFE. A cover 146 made from a water-resistant material may be useful when the pressure sensing mat 100 is used by burn patients or within an operating room environment where liquids from the patient's body or otherwise may be deposited on the cover 146. As another example, the cover 146 may include one or more layers, e.g., a first layer forming the body-facing surface 152 and a second layer formed of a fluid or moisture impermeable material. Such a configuration may wick or draw moisture from a patient's body to the moisture impermeable material.

The top cover 148 may include top cover apertures 154 and the bottom cover 150 may include bottom cover apertures 156 that may each be positioned in predetermined locations to form repeating patterns in the top and bottom covers 148 and 150. The top cover apertures 154 and the bottom cover apertures 156 may be aligned with the first apertures 118, defined by the first conductive layer 102, the second apertures 124, defined by the second conductive layer 104, and the third apertures 126 that may be defined by the insulative layer 106. The alignment of the apertures defined by the covers 154 and 156 and the first, second, and third apertures 118, 124, and 126 may form the vent 132 that may be configured to transfer fluid dispersed by the user from the body-facing surface 152 through the mat 100. In one or more embodiments, the top cover apertures 154 and the bottom cover apertures 156 may have a smaller diameter than the first, second, and third apertures 118, 124, and 126.

Figure 5:
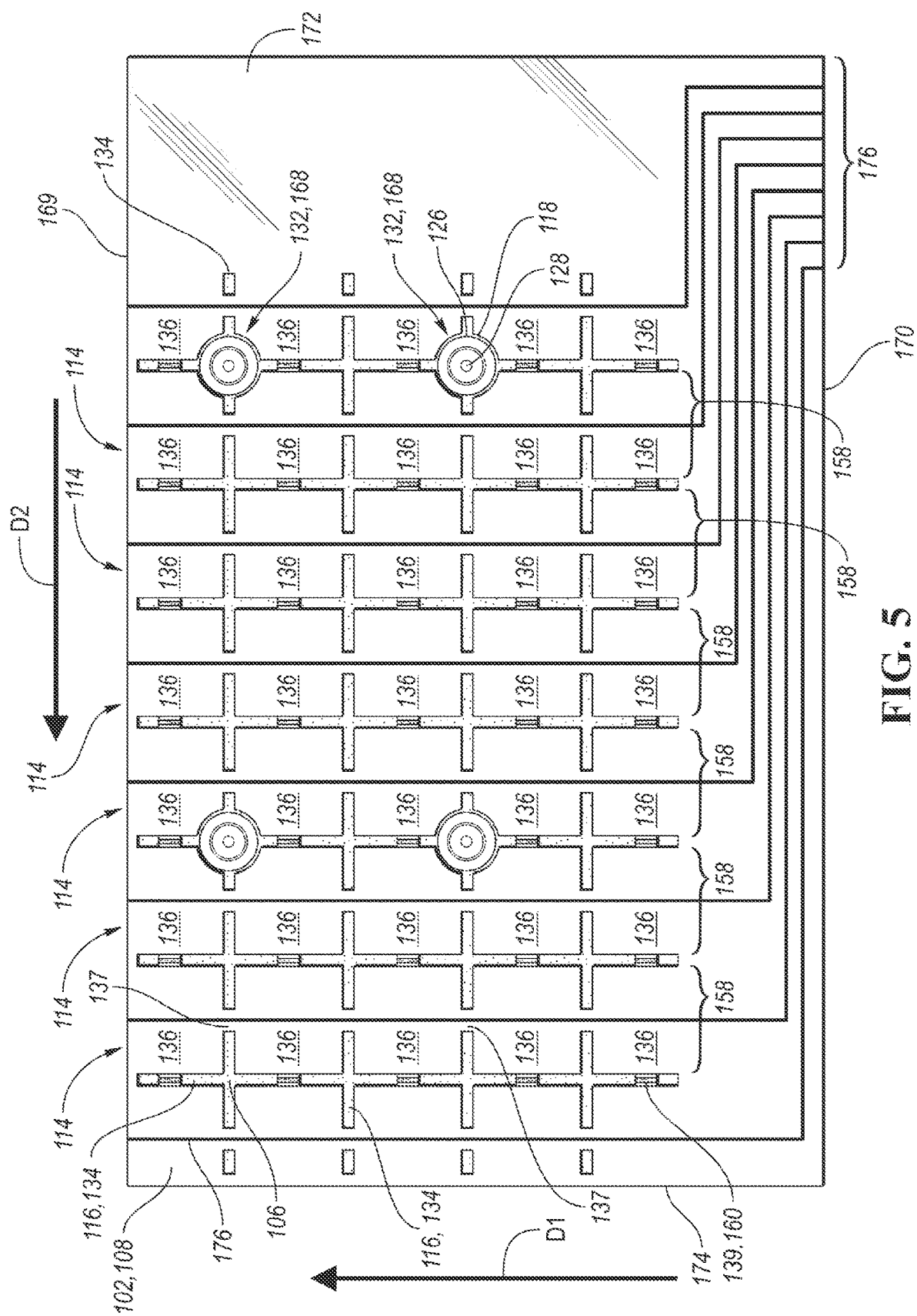
FIGS. 5 and 6A depict plan schematic views of portions of multiple embodiments of pressure sensing mats.
Figure 6A:
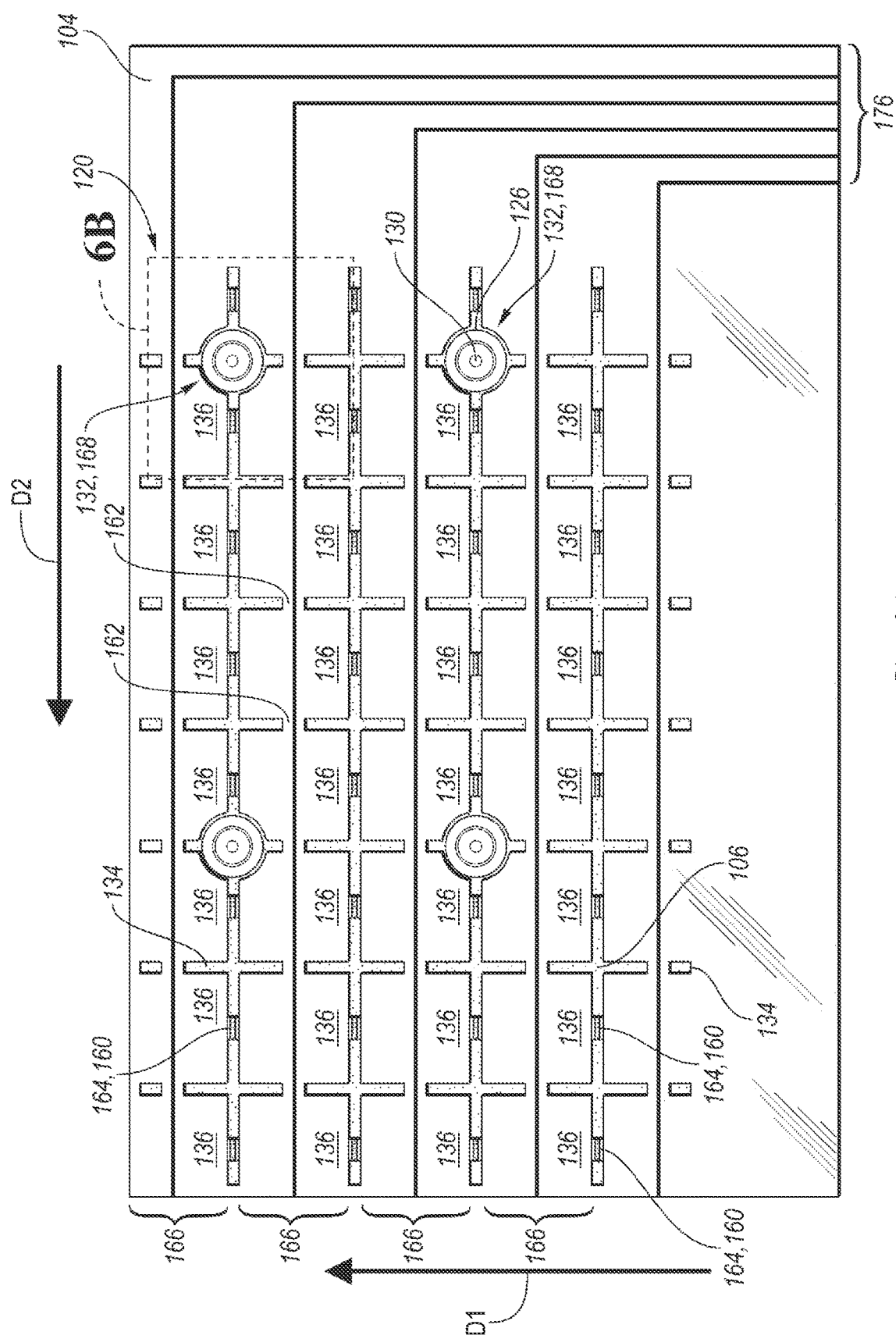

The first conductive layer 102 and the second conductive layer 104 may each be at least partially formed of a conductive metal or alloy material. As one example, the conductive layers 102, 104 may each be formed by a laminated copper material, such as 150 nm copper laminated. The laminated copper material may have a thickness ranging between 25 microns and 75 microns. As one example, Table 1 provides material properties of the 150 nm copper laminated material. In one or more embodiments, the conductive layers 102, 104 may each be formed of or include silver, aluminum, or other suitable conductive materials. The first conductive layer 102 and the second conductive layer 104 may each define interstices 134 that may form arrays of conductive cells 136 (FIGS. 5 and 6A). The conductive cells 136 of the first conductive layer 102 may be substantially aligned with the conductive cells 136 of the second conductive layer 104 to form a matrix or array of capacitors 138.

TABLE 1

| No | Criterion | Test method | Specification | Unit |
|---|---|---|---|---|
| 1 | Thickness | ISO4593 | 49 ± 8 | μ |
| 2 | Tensile Strength | ASTM D-882 | MD: 80 ± 52<br>TD: 70 ± 52 | N |
| 3 | Puncture Resistance | FTMS 101C 2065 | >40 | N |
| 4 | Lamination strength | ASTM D-882 | >300 | gr/Inch |
| 5 | Metal adhesion | Tape test with 3M 610 tape, HCTP 13 | No metal removal | |
| 6 | Copper thickness | | 150 ± 40 | nm |
| 7 | Surface Resistivity | | 0.07 – 0.21 | Ω/m |

The first conductive layer 102 and the second conductive layer 104 may each be mechanically attached to the insulative layer 106 by an adhesive. As one example, a double-sided tape (DST) may be laid along either the insulative layer 106 or the first conductive layer 102, the second conductive layer 104, or both. The insulative layer 106 may then be laid on to the first and second conductive layers 102 and 104 and vice-versa.

Figure 4:
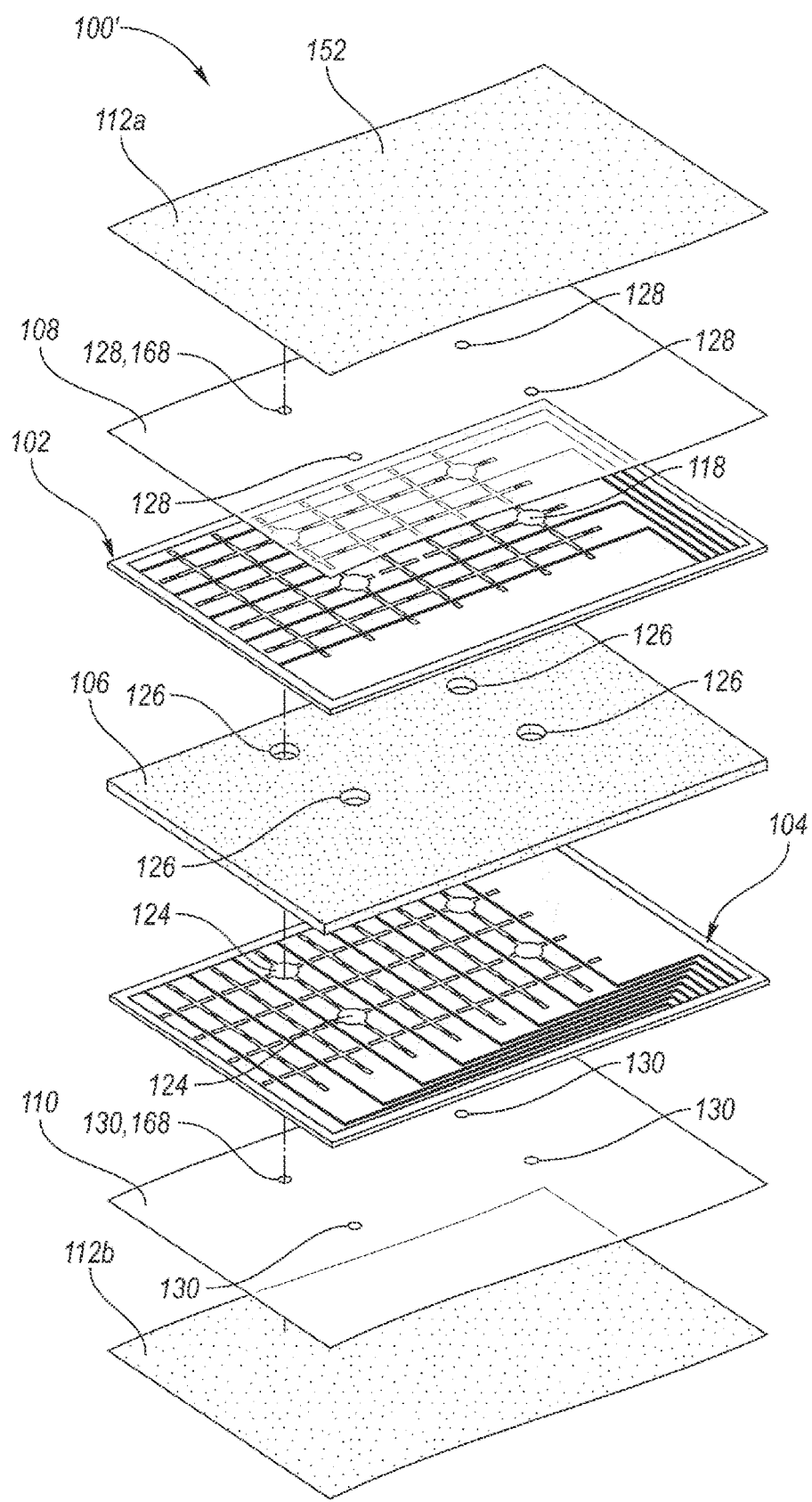

Referring to FIG. 4, an exploded schematic view of pressure sensing mat 100' according to one or more embodiments is depicted. The pressure sensing mat 100' may include the cover 112 that may include a top portion 112*a* and a bottom portion 112*b*. The cover 112 may extend the longevity of the pressure sensing mat 100 and may serve to protect the conductive layers 102, 104 from tearing or puncturing. In one or more embodiments, the cover 112 may be formed of a woven or non-woven fabric that may form the body-facing surface 152. For example, in some embodiments, the fabric that forms the body-facing surface 152 may be a wicking fabric configured to wick moisture from the patient's body to the body-facing surface 152 of the cover 112.

The first protective layer 108 may be disposed between the top portion 112*a* of the cover 112 and the first conductive layer 102 and the second protective layer 110 may be disposed between the bottom portion 112*b* of the cover 112 and the second conductive layer 104. The first protective layer 108 and the second protective layer 110 may each be formed of a waterproof material.

The cover 112 may be formed of one or more fabrics that are water and moisture permeable to facilitate transferring fluid, moisture, or both from the body-facing surface 152 to first protective layer 108 or the second protective layer 110.

The first apertures 118, the second apertures 124, and the third apertures 126, may each have a repeating pattern formed in the first conductive layer 102, the second conductive layer 104, and the insulative layer 106, respectively. For example, the portions of the first conductive layer 102, the second conductive layer 104, and the insulative layer 106, may include a number of the apertures 118, 124, and 126 that may be positioned with respect to edge portions of one or more of the layers 102, 104, and 106 and that may be spaced apart from one another by a given distance. And that portion of the one or more of the layers 102, 104, and 106 may repeat along the one or more layers 102, 104, and 106. The first and second protective layer apertures 128 and 130 may each have a repeating pattern that repeats through the first and second protective layers 108 and 110.

The first apertures 118, the second apertures 124, the third apertures 126, and the first and second protective layer apertures 128 and 130 may each have a profile or an outline formed by outer contours of the apertures 118, 124, 126, 128, and 130. As an example, the profile may define the size, such as diameter or shape of one or more portions of the apertures 118, 124, 126, 128, and 130. In one or more embodiments, the shape of the apertures 118, 124, 126, 128, and 130 may be a regular shape that is symmetrical or an irregular shape that may be asymmetrical. As an example, the shape of one or more of the apertures 118, 124, 126, 128, and 130 may be circular, semi-circular, ovular, square, rectangular, or triangular.

The first apertures 118, the second apertures 124, and the third apertures 126, may each have the same size, e.g., diameter and may be congruent with one another. In one or more embodiments, one or more of the first and second protective layer apertures 128 and 130 may have a diameter that is smaller than the diameters of one or more of the first apertures 118, the second apertures 124, and the third apertures 126. As an example, the apertures 118, 124, and 126 of the first conductive layer 102, second conductive layer 104, and insulative layer 106 may be aligned with or coaxial to the first and second protective layer apertures 128 and 130.

A number of the first apertures 118, the second apertures 124, the third apertures 126, and the first and second protective layer apertures 128 and 130 may collectively form a vent 168. In one or more embodiments, the vent 168 may extend from the first protective layer 108 through the first conductive layer 102, the second conductive layer 104, the insulative layer 106 and the second protective layer 110.

FIG. 5 illustrates a plan schematic view of the first conductive layer 102 disposed beneath the first protective layer 108 and disposed above the insulative layer 106 and the second protective layer 110. FIG. 6A illustrates a plan schematic view of the second conductive layer 104 disposed beneath the second protective layer 110 and disposed above the insulative layer 106 and the first protective layer 108.

The first conductive layer 102 may include the interstices 134 that may form the first spaced apart conductive regions 114 and the first non-conductive regions 116 that may be disposed therebetween. The first spaced apart conductive regions 114 may be formed by a number of conductive cells 136 that may extend in the first direction D1. The interstices 134 may form the first non-conductive regions 116 may each extend in the first direction D1. In one or more embodiments, the conductive cells 136 may be connected to one another by first connecting members 137 and second connecting members 139. The first connecting members 137 and the conductive cells 136, which may be aligned with one another with respect to the first direction D1, may form first conductive paths 158. The first conductive paths 158 may form one or more portions of the first spaced apart conductive regions 114.

The first conductive layer 102 may include a first edge portion 169 and a second edge portion 170 that may each extend in the second direction D2. A third edge portion 172 and a fourth edge portion 174 may each extend between the first and second edge portions 169 and 170. Conductive leads 176 may extend from the second edge portion 170 through the conductive cells 136 to the first edge portion 169. The conductive leads 176 may provide electricity to the conductive cells 136. End portions of the conductive leads 176 may be disposed at an outer periphery of the first conductive layer 102 so that the end portions may be connected, e.g., soldered to a connector (not illustrated).

The second connecting members 139 may extend between the first conductive paths 158 and may physically connect the two or more conductive cells 136 that form the first conductive paths 158. The second connecting members 139 may electrically disconnect the first conductive paths 158 from one another. As an example, the second connecting members 139 may include one or more of the discontinuities 160 that may prevent electricity from moving between adjacent ones of the first conductive paths 158. One or more of the discontinuities 160 may be formed by removing a portion of the second connecting members 139, such as by etching, cutting, or ablating. The second connecting members 139 and the interstices 134 may form one or more portions of the first non-conductive regions 116.

One or more of the number of vents 132 and 168 may overlap portions of the interstices 134. As an example, the interstices 134 may have a cross shape that may have a repeating pattern that may repeat through the first and second conductive layers 102 and 104. The cross shape of one or more of the interstices 134 may include a first leg and a second leg that may be arranged substantially orthogonally to one another. One or more of the vents 132 and 168 may be formed where the first leg and the second leg of the interstices cross one another. Placing the vent 132 and 168, or more specifically, positioning the first apertures 118 and the second apertures 124 so that they overlap portions of the interstices may limit the amount of conductive material removed to form the vents 132 and 168 and may prevent tearing of the first and second conductive layers 102 and 104 and increase the longevity of the pressure sensing mat 100 and 100'.

The second conductive layer 104 may include the second spaced apart conductive regions 120 and the second non-conductive regions 122 that may be disposed therebetween. The second spaced apart conductive regions 120 and the second non-conductive regions 122 may extend in the second direction D2. In one or more embodiments, the conductive cells 136 may be connected to one another by third connecting members 162 and fourth connecting members 164. The third connecting members 162 and the conductive cells 136, which may be aligned with one another with respect to the first direction D2, may form second conductive paths 166 that may form one or more portions of the second spaced apart conductive regions 120. As an example, the fourth connecting members 164 may include one or more of the discontinuities 160 that may prevent electricity from moving between adjacent ones of the second conductive paths 166. One or more of the discontinuities 160 may be formed by removing a portion of the second connecting members 139, such as by etching, cutting, or ablating. The fourth connecting members 164 and the interstices 134 may form one or more portions of the second non-conductive regions 122.

Figure 6B:
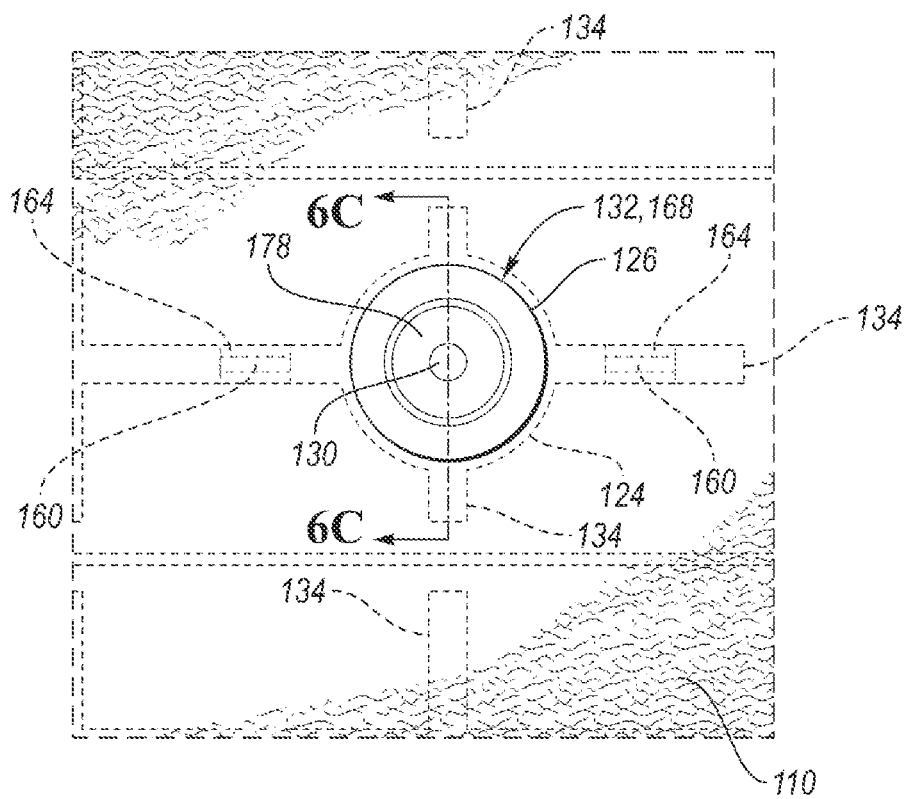
FIG. 6B depicts a detail plan schematic view taken from region 6B in FIG. 6A.

FIG. 6B illustrates a portion of the second conductive layer 104. The vent 132 may be formed by a sealed circumference formed of circumferential areas of the first apertures 118, the second apertures 124, and the third apertures 126 and the vent 168 may be formed by a sealed circumference formed of circumferential areas of the first apertures 118, the second apertures 124, and the third apertures 126 and the first and second protective layer apertures 128 and 130. In one or more embodiments, the sealed circumference may be formed by the circumferential areas of the first apertures 118, the second apertures 124, and the third of aperture 126 and the first and second protective layer apertures 128 and 130 that are co-minglingly joined. As one example, the circumferential areas may be fixed to one another by a molecular bond by melting one or more of the circumferential areas to the other circumferential areas.

The circumferential areas of a pair of a first protective layer aperture 128 and a second protective layer aperture 130 may form a reservoir such as a recessed pocket 178. The recessed pocket 178 may be configured to collect fluid or vapor received from or through the body-facing surface 152 and transport the fluid or vapor through the first and second protective layer apertures 128 and 130.

Figure 6C:
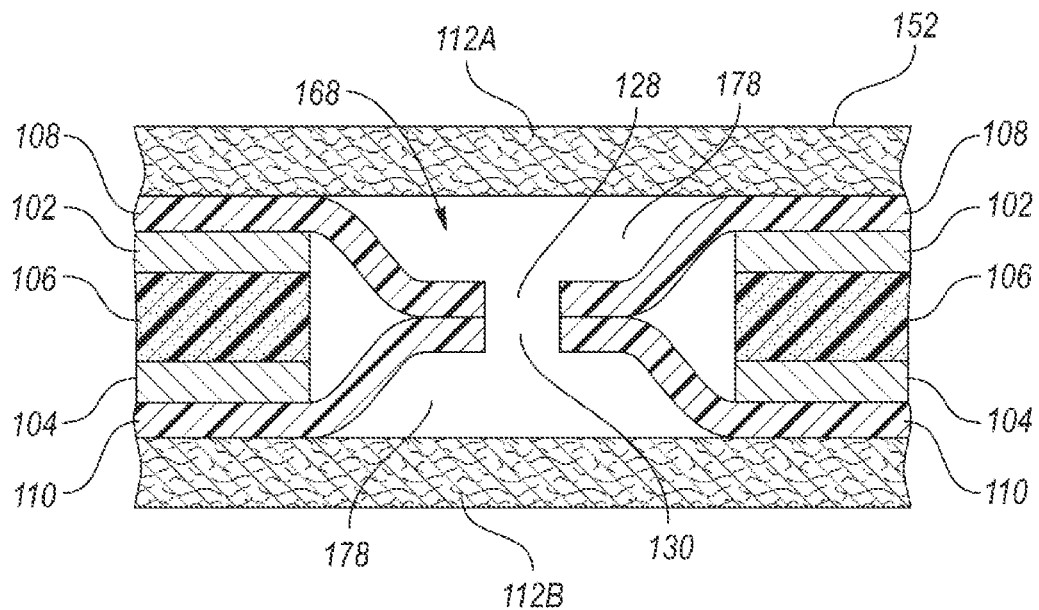
FIG. 6C depicts a detail cross-sectional, and schematic view taken along lines 6C in FIG. 6B.

FIG. 6C illustrates a detail cross-sectional, schematic view taken along lines 6C in FIG. 6B. The top portion 112a of the cover 112 lies along the first protective layer 108 and the bottom portion 112b of the cover 112 lies along the second protective layer 110. The first protective layer 108 and the second protective layer 110 may each define the first protective layer apertures 128 and the second protective layers apertures 130, respectively. Circumferential areas of the first protective layer apertures 128 and the second protective layers apertures 130 may be co-minglingly joined to one another to form a portion of the vent 168. Portions of the first protective layer 108 and the second protective layer 110 may form the recessed pocket 178. The first protective layer 108 may lie along the first conductive layer 102 and the second protective layer 110 may lie along the conductive layer 110. The first conductive layer 102 and the second conductive layer 104 may each lie along the insulative layer 106.

FIG. 7 depicts a fragmented, exploded, perspective view of a portion of an exemplary pressure sensing mat such as one of the first conductive layer 102 or the second conductive layer 104. In one or more embodiments, one or more of the conductive layers 102, 104 may include plastic laminations 180 that may be disposed on a first side, second side, or both sides of the laminated conductive material 182. The plastic laminations 180 may include one or more polymeric materials such as polyethylene (PE) or polyethylene terephthalate (PET). As an example, the PET layer 184 may be disposed between one side of the laminated conductive material 182 and a layer of the PE layer 186. The plastic laminations 180 may be melted to cover or enclose the laminated conductive material 182.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A pressure sensing mat comprising:
a first conductive layer including a first plurality of spaced apart conductive regions and a first plurality of non-conductive regions therebetween, the first plurality of spaced apart conductive regions and the first plurality of non-conductive regions extending in a first direction, the first conductive layer defining a first aperture;
a second conductive layer including a second plurality of spaced apart conductive regions and a second plurality of non-conductive regions therebetween, the second plurality of spaced apart conductive regions and the second plurality of non-conductive regions extending in a second direction different than the first direction, the second conductive layer defining a second aperture; and
an insulative layer disposed between the first conductive layer and the second conductive layer and defining a third aperture, the first aperture, the second aperture, and the third aperture are aligned with each other such that the first aperture, the second aperture, and the third aperture form a vent through the first conductive layer and the second conductive layer and the insulative layer, the first and second pluralities of spaced apart conductive regions do not span the third aperture.

2. The pressure sensing mat of claim 1, wherein the first aperture includes a first pattern of apertures, the second aperture includes a second pattern of apertures, and the third aperture includes a third pattern of apertures, the first pattern of apertures, the second pattern of apertures, and the third pattern of apertures forming a plurality of vents through the first conductive layer and the second conductive layer and the insulative layer, the first and second pluralities of spaced apart conductive regions do not span the third pattern of apertures.

3. The pressure sensing mat of claim 2, wherein the first pattern of apertures, the second pattern of apertures, and the third pattern of apertures are first, second and third repeating patterns, respectively.

4. The pressure sensing mat of claim 1, wherein the first aperture, the second aperture, and the third aperture each have first, second, and third profiles, respectively.

5. The pressure sensing mat of claim 4, wherein the first profile, the second profile, and the third profile are substantially congruent to one another.

6. The pressure sensing mat of claim 1, further comprising:
a first protective layer adjacent to the first conductive layer, the first protective layer defining a first protective layer aperture; and
a second protective layer adjacent to the second conductive layer, the second protective layer defining a second protective layer aperture.

7. The pressure sensing mat of claim 6, wherein the first protective layer and the second protective layer are first and second outer layers, respectively.

8. A pressure sensing mat comprising:
a first conductive layer including a first plurality of spaced apart conductive regions and a first plurality of non-conductive regions therebetween, the first plurality of spaced apart conductive regions and the first plurality of non-conductive regions extending in a first direction, the first conductive layer defining a first aperture;

a second conductive layer including a second plurality of spaced apart conductive regions and a second plurality of non-conductive regions therebetween, the second plurality of spaced apart conductive regions and the first plurality of non-conductive regions extending in a second direction different than the first direction, the second conductive layer defining a second aperture;

an insulative layer disposed between the first and second conductive layers and defining a third aperture, the first and second pluralities of spaced apart conductive regions do not span the third aperture;

a first protective layer adjacent to the first conductive layer, the first protective layer defining a first protective layer aperture; and a second protective layer adjacent to the second conductive layer, the second protective layer defining a second protective layer aperture.

9. The pressure sensing mat of claim 8, wherein the first protective layer aperture and the second protective layer aperture are diametrically smaller than the first aperture, the second aperture, and the third aperture.

10. The pressure sensing mat of claim 8, wherein the first, second, and third apertures and the first and second protective layer apertures form a vent having a sealed circumference configured to inhibit penetration of water and/or vapor into the first conductive layer and the second conductive layer and the insulative layer.

11. The pressure sensing mat of claim 10, wherein the sealed circumference includes co-minglingly joined circumferential areas of the first aperture, the second aperture, and the third aperture and the first protective layer aperture and the second protective layer aperture.

12. The pressure sensing mat of claim 10, wherein the sealed circumference includes ultrasonically soldered circumferential areas of the of the first aperture, the second aperture, and the third aperture and the first protective layer aperture and the second protective layer aperture.

13. The pressure sensing mat of claim 8, wherein the first protective layer aperture includes a first circumference and the second protective layer aperture includes a second inner circumference fixed to the first circumference.

14. The pressure sensing mat of claim 13, wherein the first circumference and the second circumference are coaxial to the third aperture.

15. The pressure sensing mat of claim 14, wherein the first circumference and the second circumference collectively form a reservoir configured to transport water and/or vapor.

16. The pressure sensing mat of claim 8, wherein the first aperture has a first circumference, the second aperture has a second circumference and the third aperture has a third circumference, wherein the third circumference is fixed to at least one of the first circumference or the third circumference.

17. The pressure sensing mat of claim 8, wherein the first aperture includes a first pattern of apertures, the second aperture includes a second pattern of apertures, and the third aperture includes a third pattern of apertures, the first protective layer aperture includes a first protective layer pattern of apertures, the second protective layer aperture includes a second protective layer pattern of apertures, the first, second and third patterns of apertures and the first and second protective layer patterns of apertures forming a plurality of vents through the first and second protective layers, the first conductive layer and the second conductive layer and the insulative layer, the first and second pluralities of spaced apart conductive regions do not span the third pattern of apertures.

18. A pressure sensing mat comprising:
a first conductive layer including a first plurality of spaced apart conductive regions and a first plurality of non-conductive regions therebetween, the first plurality of spaced apart conductive regions and the first plurality of non-conductive regions extending in a first direction, the first conductive layer defining a first aperture;

a second conductive layer including a second plurality of spaced apart conductive regions and a second plurality of non-conductive regions therebetween, the second plurality of spaced apart conductive regions and the first plurality of non-conductive regions extending in a second direction different than the first direction, the second conductive layer defining a second aperture;

an insulative layer disposed between the first and second conductive layer and defining a third aperture;

a first protective layer adjacent the first conductive layer and defining a first protective layer aperture;

a second protective layer adjacent the second conductive layer and defining a second protective layer aperture, the first aperture, the second aperture, and the third aperture and the first and second protective layer apertures collectively form a vent, the first and second pluralities of spaced apart conductive regions do not span the third aperture; and a cover at least partially covering the first protective layer and formed of moisture permeable material configured to transport moisture and/or a fluid from an outer surface of the cover to the vent.

19. The pressure sensing mat of claim 18, wherein the first and second protective layers are moisture impermeable.

20. The pressure sensing mat of claim 18, wherein the first protective layer includes a recessed pocket configured to transport the moisture and/or the fluid.

* * * * *